United States Patent [19]

Singleton et al.

[11] Patent Number: 6,100,304
[45] Date of Patent: Aug. 8, 2000

[54] PROCESSES AND PALLADIUM-PROMOTED CATALYSTS FOR CONDUCTING FISCHER-TROPSCH SYNTHESIS

[75] Inventors: Alan H. Singleton, Baden; Rachid Oukaci, Gibsonia; James G. Goodwin, Cranberry Township, all of Pa.

[73] Assignee: Energy International Corportion, Pittsburgh, Pa.

[21] Appl. No.: 09/320,401

[22] Filed: May 26, 1999

Related U.S. Application Data

[60] Provisional application No. 60/086,848, May 27, 1998.

[51] Int. Cl.$^7$ .............................. C07C 27/00; B01J 23/40; B01J 20/00
[52] U.S. Cl. .......................... 518/715; 518/700; 502/326; 502/414
[58] Field of Search ..................... 518/700, 715; 502/326, 514

[56] References Cited

U.S. PATENT DOCUMENTS

| | | |
|---|---|---|
| 3,943,052 | 3/1976 | Kmak et al. . |
| 4,079,072 | 3/1978 | Finch . |
| 4,133,841 | 1/1979 | Maule et al. . |
| 4,219,445 | 8/1980 | Finch . |
| 4,235,754 | 11/1980 | Chester . |
| 4,252,736 | 2/1981 | Haag et al. . |
| 4,260,518 | 4/1981 | Katzer et al. . |
| 4,385,193 | 5/1983 | Bijwaard et al. . |
| 4,403,044 | 9/1983 | Post et al. . |
| 4,423,265 | 12/1983 | Chu et al. . |
| 4,460,710 | 7/1984 | Sapienza et al. ................ 518/700 |
| 4,523,047 | 6/1985 | Chester et al. . |
| 4,595,703 | 6/1986 | Payne et al. . |
| 4,637,993 | 1/1987 | van Erp . |
| 4,684,756 | 8/1987 | Derr, Jr. et al. . |
| 4,686,313 | 8/1987 | Bell et al. . |
| 4,863,890 | 9/1989 | Koll . |
| 4,880,763 | 11/1989 | Eri et al. . |
| 4,908,341 | 3/1990 | Pruden et al. . |
| 5,023,277 | 6/1991 | McAteer . |
| 5,102,851 | 4/1992 | Eri et al. . |
| 5,116,800 | 5/1992 | Williamson et al. . |
| 5,206,202 | 4/1993 | Lachman et al. . |
| 5,461,022 | 10/1995 | Dosch et al. . |
| 5,939,350 | 8/1999 | Singleton et al. ................ 502/230 |

FOREIGN PATENT DOCUMENTS

| | | |
|---|---|---|
| 454256B1 | 10/1991 | European Pat. Off. . |
| 533227B1 | 3/1993 | European Pat. Off. . |
| 579330B1 | 5/1996 | European Pat. Off. . |
| 736326A1 | 9/1996 | European Pat. Off. . |

*Primary Examiner*—Shailendra Kumar
*Assistant Examiner*—J. Parsa
*Attorney, Agent, or Firm*—Fellers, Snider, Blankenship, Bailey & Tippens, P.C.

[57] ABSTRACT

A process for hydrocarbon synthesis comprising the step of reacting a synthesis gas in the presence of a cobalt catalyst promoted with palladium.

20 Claims, No Drawings

PROCESSES AND PALLADIUM-PROMOTED CATALYSTS FOR CONDUCTING FISCHER-TROPSCH SYNTHESIS

This application claims the benefit of U.S. provisional application Ser. No. 60/086,848 filed May 27, 1998.

The Government of the United States of America has rights to this invention pursuant to Contract No. DE-AC22–92PC92108 awarded by the U.S. Department of Energy.

BACKGROUND OF THE INVENTION

1. Technical Field

This invention relates generally to catalysts and processes for conducting Fischer-Tropsch synthesis.

2. Background

Synthesis gas, or "syngas," is a mixture consisting primarily of hydrogen and carbon oxides. Syngas is produced during coal gasification. Processes are also well known for obtaining syngas from other hydrocarbons, including natural gas. U.S. Pat. No. 4,423,265 to Chu et al. notes that the major processes for producing syngas depend either upon the partial combustion of the hydrocarbon fuel with an oxygen-containing gas or upon the reaction of the fuel with steam, or on a combination of these two reactions. U.S. Pat. No. 5,324,335 to Benham et al., explains the two primary methods (i.e., steam reforming and partial oxidation) for producing syngas from methane. The entire disclosure of each of U.S. Pat. Nos. 4,423,265 and 5,324,335 is incorporated herein by reference. The Encyclopedia of Chemical Technology, Second Edition, Volume 10, pages 3553–433 (1966), Interscience Publishers, New York, N.Y. and Third Edition, Volume 11, pages 410–446 (1980), John Wiley and Sons, New York, N.Y. is said by Chu et al. to contain an excellent summary of gas manufacture, including the manufacture of synthesis gas.

It has long been recognized that syngas can be converted to liquid hydrocarbons by the catalytic hydrogenation of carbon monoxide. The general chemistry of the much studied Fischer-Tropsch synthesis process is as follows:

$$CO + 2H_2 \rightarrow (-CH_2-) + H_2O \quad (1)$$

$$2CO + H_2 \rightarrow (-CH_2-) + CO_2 \quad (2)$$

The types and amounts of reaction products, i.e., the lengths of carbon chains, obtained via Fischer-Tropsch synthesis vary dependent upon process kinetics and choice of catalyst.

Many attempts at providing effective catalysts for selectively converting syngas to liquid hydrocarbons have previously been disclosed. U.S. Pat. No. 5,248,701 to Soled et al., presents an overview of relevant prior art. The entire disclosure of U.S. Pat. No. 5,248,701 is incorporated herein by reference.

The two most popular types of catalysts heretofore used in Fischer-Tropsch synthesis are iron-based catalysts and cobalt-based catalysts. U.S. Pat. No. 5,324,335 to Benham et al. discusses the fact that iron-based catalysts, due to their high water gas shift activity, favor the overall reaction shown in (2) above, while cobalt-based catalysts tend to favor the overall reaction of scheme (1).

Recent advances have provided a number of catalysts active in Fischer-Tropsch synthesis. Besides iron and cobalt, other Group VIII metals, particularly ruthenium, are known Fischer-Tropsch catalysts.

The current practice is to support such catalysts on porous inorganic refractory oxides. Particularly preferred supports include silica, alumina, silica-alumina, and titania. In addition, other refractory oxides selected from Groups III, IV, V, VI and VIII may be used as catalyst supports.

The prevailing practice is also to add promoters to the supported catalyst. Promoters can include ruthenium (when not used as the primary catalyst component), rhenium, hafnium, cerium, and zirconium. Promoters are known to increase the activity of the catalyst, sometimes rendering the catalyst three to four times as active as its unpromoted counterpart.

Contemporary cobalt catalysts are typically prepared by impregnation of the catalytic material upon the support. As described in U.S. Pat. No. 5,252,613 to Chang et al., a typical catalyst preparation may involve impregnation, by incipient wetness or other known techniques of, for example, a cobalt nitrate salt onto a titania, silica or alumina support, optionally followed or preceded by impregnation with a promoter material. Excess liquid is removed and the catalyst precursor is dried. Following drying or as a continuation thereof, the catalyst is calcined to convert the salt or compound to its corresponding oxide(s). The oxide is then reduced by treatment with hydrogen or a hydrogen-containing gas for a period of time sufficient to substantially reduce the oxide to the elemental or catalytic form of the metal. U.S. Pat. No. 5,498,638 to Long points to U.S. Pat. Nos. 4,673,993, 4,717,702, 4,477,595, 4,663,305, 4,822,824, 5,036,032, 5,140,050, and 5,292,705 as disclosing well known catalyst preparation techniques.

The entire disclosure of each of the U.S. patents mentioned in the previous paragraph is incorporated herein by reference.

Fischer-Tropsch synthesis has primarily been conducted in fixed bed reactors, gas-solid reactors, and gas-entrained fluidized bed reactors, fixed bed reactors being the most utilized. U.S. Pat. No. 4,670,472 to Dyer et al. provides a bibliography of several references describing these systems. The entire disclosure of U.S. Pat. No. 4,670,472 is incorporated herein by reference.

More recently, however, attention has been directed to conducting Fischer-Tropsch synthesis in three-phase slurry reactors. Three phase reactions involve the introduction of a fluidizing gas into a reactor containing catalyst particles slurried in a liquid. Particularly useful in Fischer-Tropsch processes is the slurry bubble column reactor (SBCR). In a SBCR, catalyst particles are slurried in liquid hydrocarbons within a reactor chamber, typically a tall column. Syngas is then introduced at the bottom of the column through a distributor plate, which produces small gas bubbles. The gas bubbles migrate up and through the column, causing a beneficial turbulence, while reacting in the presence of the catalyst to produce liquid and gaseous hydrocarbon products. Gaseous products are captured at the top of the SBCR, while liquid products are recovered through a filter which separates the liquid hydrocarbons from the catalyst fines. U.S. Pat. Nos. 4,684,756, 4,788,222, 5,157,054, 5,348,982, and 5,527,473 reference this type of system and provide citations to pertinent patent and literature art. The entire disclosure of each of these patents is incorporated herein by reference.

Using a SBCR to conduct Fischer-Tropsch synthesis has certain recognized advantages. As noted by Rice et al. in U.S. Pat. No. 4,788,222, advantages of a slurry process over a fixed bed process include better control of the exothermic heat produced during the reactions and better maintenance of catalyst activity by allowing continuous recycling, recovery and rejuvenation procedures to be implemented. U.S. Pat. Nos. 5,157,054, 5,348,982, and 5,527,473 also discuss advantages flowing from the use of a SBCR.

Heretofore, catalyst particle size has not been deemed to be a critical parameter in SBCRs. It is desired that the catalyst particle be reasonably filterable, but also easily dispersible. The art suggests that the particle sizes of 1–200 microns meet these requirements. (See Chang, Col. 5).

Notwithstanding the research and development heretofore conducted, Fischer-Tropsch synthesis in a three phase slurry bubble column reactor is by no means a refined procedure. The process remains expensive, owing in part to the significant cost of promoted catalysts in the current state of the art. Environmental concerns also come into play, not only with respect to the operation of a SBCR, but also with regard to the preparation of catalysts, which involves the use of organic solvents.

The present invention encompasses certain discoveries that have resulted in a more rate efficient, more selective, environmentally friendly, and more cost efficient process for conducting Fischer-Tropsch synthesis, particularly in a slurry bubble column reactor.

SUMMARY OF THE INVENTION

The present invention involves the preparation and use of palladium promoted cobalt catalysts for Fischer-Tropsch synthesis. Palladium is one of the most economical members of the family of noble metals capable of promoting cobalt reducibility. Heretofore, though, the use of palladium as a promoter for cobalt-based Fischer-Tropsch catalysts has not been thought to be very advantageous (see e.g., U.S. Pat. No. 5,102,851, the entire disclosure of which is incorporated herein by reference). On the contrary, it has been suggested that the addition of palladium to a cobalt catalyst, compared to the addition of platinum, iridium or rhodium, results in slight or no improvement in catalyst activity for Fischer-Tropsch synthesis.

But it has been discovered in connection with the present invention that palladium promotion of cobalt catalysts can indeed provide a significant activity enhancement. Moreover, in accordance with the present invention, results obtained using palladium-promoted cobalt catalysts in a slurry bubble column reactor unexpectedly were comparable to the results obtained with ruthenium-promoted catalysts. In addition, temperature programmed reduction studies have shown that palladium addition has a positive effect on cobalt reducibility, similar to the effect provided by ruthenium addition.

Additional inventive aspects are discussed and/or demonstrated hereinbelow. A better understanding of the present invention, its several aspects, and its objects and advantages will be apparent to those skilled in this art from the following detailed description wherein there are described only the preferred embodiments of the invention, simply by way of illustration of the best mode contemplated for carrying out the invention. As will be apparent, the invention is capable of modifications in various respects, all without departing from the invention. Accordingly, the description should be regarded as illustrative in nature and not as restrictive.

DETAILED DESCRIPTION OF THE PREFERRED EMBODIMENTS

Catalyst Compositions

The present invention provides supported cobalt catalysts which are well suited for use in Fischer-Tropsch synthesis. These catalysts are particularly well suited for use in slurry bubble column reactor (SBCR) process. The general catalyst compositions provided by the present invention comprise cobalt with a palladium promoter, preferably supported on γ-alumina or doped γ-alumina.

The palladium-promoted catalysts preferably comprise (per 100 parts by weight of support): from about 10 to about 65 parts by weight (pbw) cobalt; from about 0.25 to about 9 pbw palladium; and from about 0.1 to about 8 pbw potassium (when present). The palladium-promoted catalyst will most preferably comprise (per 100 pbw of support): from about 17 to about 45 pbw cobalt; from about 0.5 to about 3.5 pbw palladium; and from about 0.2 to about 1.0 pbw potassium (when present).

Although other types of supports, including other types of alumina supports, can be used, examples of support materials particularly preferred for use in the present invention include: (a) γ-alumina obtained by calcination of CATAPAL B or PURAL SB boehmite from Condea/Vista or γ-aluminas having similar characteristics and (b) γ-alumina doped with at least one of titanium, lanthanum, barium, calcium, vanadium, tungsten, or potassium.

The support will most preferably have: very low amounts of impurities, especially sulfur (preferably less than 100 ppm sulfur); a spheroidal shape with an average particle size ranging from about 10 to about 150 μm; a BET surface area, after calcination, ranging from about 200 to about 260 m$^2$/g; and from 0 to about 1000 ppm titanium added prior to crystallization. In the case of doped aluminas, the dopant will preferably be added prior to crystallization or to the boehmite prior to calcination and will preferably be present in an amount in the range of from about 0.01% to about 10% (most preferably from about 0.1% to about 5%) by weight based on the total weight of the support.

The CATAPAL B and PURAL SB aluminas from Condea/Vista are obtained by a manufacturing process which typically results in a material having very low levels of the impurities commonly found in aluminas derived from bauxite. A spray drying process used in the final stage of the preparation process desirably provides a high surface area, a high porosity, and a spheroidicity which are particularly desirable for the present invention. The commercially supplied alumina (pre- or non-doped) is preferably sieved to remove fines and large particles and to thus provide the desired particle size range. The sieved alumina is then calcined at approximately 400–700° C., preferably about 500°, for about 5–24 hours, preferably about 10 hours, in order to convert the alumina from the boehmite state to a γ-alumina product having a surface area of from about 200 to about 260 m$^2$/g. The desired calcination temperature is preferably reached by slowly heating the system at a rate of about 0.5–2.0° C./minute.

When a doped support is desired, the commercially supplied alumina is preferably first sieved to remove fines and large particles and then impregnated with a desired dopant nitrate using a totally aqueous impregnation method. The support is then dried with moderate mixing for about 5–24 hours at approximately 80–130° C. to remove solvent water. The support is then calcined (preferably following the same procedure described above for non-doped supports) to obtain a suitable surface area (preferably from about 200 to about 260 m$^2$/g).

It has been discovered that, for cobalt catalysts used in Fischer-Tropsch synthesis in slurry bubble column reactors, the proper preparation and use of a preformed, spheroidal, γ-alumina support having a high surface area and sphere sizes of from about 20 to about 150 μm provides a cobalt catalyst which is much more attrition resistant than cobalt catalysts utilizing other types of oxide supports (e.g, silica)—even when these other supports are spheroidal. Further, added improvement in attrition resistance is obtained by incorporating a lanthana ($La_2O_3$) promoter. When used, lanthana will preferably be present in an amount in the range of from about 0.5% to about 5% by weight based on the total weight of the catalyst.

The particular support used in a cobalt catalyst was found, in both a fixed bed and a slurry bubble column reactor system, to play a major role in influencing overall hydrocarbon production rate with little or no effect on catalyst selectivity. For the supports tested, catalyst activities varied in the following order: $Al_2O_3>SiO_2>>TiO_2$. With respect to other alumina supports, our tests and comparisons with literature data reveal that the source of the alumina and the pretreatment procedures used play major roles in determining the performance of the resulting cobalt-based Fischer-Tropsch catalysts.

$TiO_2$ supported Co catalysts were found to have poor Fischer-Tropsch properties in both fixed bed and the SBCR systems. One primary problem encountered with $TiO_2$ supports is that they have low surface areas and therefore do not readily retain high cobalt loadings. Another problem is that they do not appear to be robust enough for use in SBCR systems. Titania has also been shown to be unstable under certain regeneration conditions.

Compared to titania, γ-alumina derived from CATAPAL B boehmite has a much higher surface area and pore volume.

Although having relatively high surface areas, silica-supported cobalt catalysts provide low Fischer-Tropsch performance. Silica-supported cobalt catalysts are unstable in reaction conditions, such as those usually encountered in Fischer-Tropsch reaction systems, where a significant amount of water is present. The formation of cobalt-silica compounds under these conditions is believed to cause this lower performance. To prevent or at least slow down silicate formation, the silica surface must typically be coated with oxide promoters, such as $ZrO_2$, prior to cobalt impregnation.

Catalyst Preparation

The components of the preferred catalyst are preferably added to the support either by totally aqueous impregnation or, most preferably, by totally aqueous co-impregnation. In addition to being safer, more economical, and environmentally friendly, totally aqueous impregnation produces a highly disperse catalytic phase in which the promoter(s) is/are in intimate contact with the cobalt component. This intimate contact significantly enhances the reducibility of the cobalt catalyst and increases catalyst activity.

Due to the shortcomings of coprecipitation processes, impregnation techniques have become the preferred means of putting cobalt and its promoters onto porous supports. Catalyst preparation by impregnation has normally been conducted by contacting a porous support, such as alumina, with a solution of the relevant metal, and then removing the solvent by evaporation (drying). The metal compound solution can be either an aqueous or an organic solution. When incorporating multiple components on a porous support, several impregnation steps (such as sequential impregnation of the active metal (e.g. cobalt) and promoters, with or without calcination of the catalyst precursors after the first metal impregnation, or co-impregnation of the metals in several steps with or without calcination of the catalyst precursor after each step) can be used. An intimate contact between the active metal and the promoters and a uniform distribution of all of the metals within the porous structure of the support are generally sought when impregnation techniques are used.

The totally aqueous impregnation of cobalt and the desired promoters is preferably accomplished by the steps of: (a) calcining the alumina support at approximately 400–700° C. for about 5–24 hours; (b) impregnating the support with an aqueous solution of cobalt nitrate, or of cobalt nitrate and one or more promoter compounds (preferably one or more promoter-nitrates and/or promoter-chlorides, most preferably promoter-nitrates), using a sufficient quantity of the solution to achieve incipient wetness with a desired loading of cobalt and the desired promoter(s); (c) drying the resulting catalyst precursor for about 5–24 hours at approximately 80–130° C., with moderate mixing, to remove solvent water and obtain a dried catalyst; and (d) calcining the dried catalyst in air or nitrogen by slowly raising its temperature at a rate of about 0.5–2.0° C. per minute to approximately 250–400° C. and then holding for at least 2 hours to obtain the oxide form of the catalyst. Multiple impregnation/coimpregnation steps (b) can be used when higher cobalt loadings are desired.

The palladium compound presently preferred for use in this aqueous impregnation process is palladium (II) nitrate [$Pd(NO_3)_2 \times H_2O$].

In another example, a doubly promoted cobalt catalyst is prepared in a similar fashion using potassium nitrate [$KNO_3$] dissolved in the same solution containing the cobalt and palladium precursors.

Catalyst Activation

To provide optimum performance, it is presently preferred that the catalyst be activated/reduced in a hydrogen-containing gas by slowly increasing the temperature of the catalyst, preferably at a rate of about 0.5–2.0° C./minute, to approximately 250–400° C. (preferably about 5 350° C.) and holding at the desired temperature for at least 2 hours. After reduction, the catalyst is preferably cooled in flowing nitrogen.

The reducing gas preferably comprises from about 1% to 100% by volume hydrogen with the remainder (if any) being an inert gas, typically nitrogen. The reducing gas is preferably delivered at a rate of about 2–4 (preferably about 3) liters per hour per gram of catalyst. The reduction procedure is preferably conducted in a fluidized bed reactor. The reduction procedure is most preferably conducted at conditions (i.e., temperature, flow rate, hydrogen concentration, etc.) effective to ensure that a very low water vapor partial pressure is maintained during the procedure.

This activation procedure enhances the performance of substantially all of the catalysts produced and used in the present invention. It is presently most preferred that the partial pressure of water vapor in the activation system be maintained below and most preferably below 0.1 atmospheres.

The Fischer-Tropsch Reaction Process

The catalysts prepared and activated in accordance with the present invention can be employed in generally any Fischer-Tropsch synthesis process. Where applicable (e.g., for SBCR systems, continuous stirred tank reactor (CSTR) systems, fixed bed systems, etc.), the catalyst will preferably be slurried in a Fischer-Tropsch wax or in a synthetic fluid (e.g., a $C_{30}$ to $C_{50}$ range isoparaffin polyalphaolefin such as that available from Chevron under the name SYNFLUID) having properties similar to the Fischer-Tropsch wax at reaction conditions. The catalyst slurry will preferably have a catalyst concentration in the range of from about 5% to about 40% by weight based on the total weight of the slurry.

The synthesis gas feed used in the reaction process will preferably have a $CO:H_2$ volume ratio of from about 0.5 to about 3.0 and will preferably have an inert gas (i.e., nitrogen, argon, or other inert gas) concentration in the range of from 0 to about 60% by volume based on the total volume of the feed. The inert gas is preferably nitrogen.

Prior to initiating the reaction process, the activated catalyst will most preferably be maintained in an inert atmosphere. Before adding the catalyst thereto, the slurry fluid will preferably be purged with nitrogen or other inert gas to remove any dissolved oxygen. The slurry composition will also preferably be transferred to the reaction system under an inert atmosphere.

A particularly preferred SBCR reaction procedure employed in the present invention comprises the steps of: (a) filling the SBCR, under an inert atmosphere, with the activated catalyst slurry; (b) heating and pressurizing the SBCR, under an inert atmosphere, to desired pretreatment conditions (preferably a temperature in the range of from about 220° to about 250° C. and a pressure in the range of from about 50 to about 500 psig); (c) replacing the inert gas with hydrogen and holding the system at these conditions for from about 2 to about 20 hours; (d) purging the system with inert gas and lowering the reaction system temperature, if necessary, to a point at least about 20 10° C. below the desired reaction temperature; (e) carefully replacing the inert gas with the desired synthesis gas; and (f) heating and pressurizing the reaction system, as necessary, to a desired operating temperature, preferably in the range of from about 190° to about 300° C., and a desired operating pressure, preferably in the range of from about 50 to about 900 psig.

Palladium Promoted Cobalt Catalysts

The present invention provides palladium promoted cobalt catalysts which unexpectedly and surprisingly yield very desirable results in Fischer-Tropsch synthesis processes conducted in fixed bed, SBCR, and other reactor systems. Cobalt catalysts supported on carriers such as alumina, silica or titania are very active for Fischer-Tropsch synthesis when the cobalt is in its reduced state. Noble metal promoters are often used to improve the reducibility of the cobalt, which results in improved activity of the catalyst for Fischer-Tropsch synthesis. Other promoters, such as potassium, may optionally be added to improve other catalyst properties such as selectivity, stability, etc.

The use of palladium as a promoter in cobalt-based, Fischer-Tropsch catalysts has not heretofore been recognized as providing acceptable activity for either fixed bed or SBCR applications. On the contrary, U.S. Pat. No. 5,102,851 (the entire disclosure of which is incorporated herein by reference), states that addition of a "non-Fischer-Tropsch" metal such as palladium to a cobalt catalyst results in only slight or no improvement in catalyst activity for Fischer-Tropsch synthesis over nonpromoted catalysts. In addition, FIG. 7 of the same patent shows that carbon monoxide conversion decreases with increasing palladium loading to a level below that obtained with a catalyst containing no palladium at all.

EXAMPLE 1

The following catalysts were prepared as indicated:

Catalyst Formulation EI.31
Composition: 20 pbw Co
  0.5 pbw Pd
  79.5 pbw γ-alumina support
Amount produced: 150 g
Preparation Procedure:
Vista CATAPAL B γ-alumina was calcined at 500° C. for 10 hours (1° C./min to 500° C.) and sieved to >38 microns and <88 microns (400–170 mesh). Then the support was impregnated with an aqueous solution of Co nitrate $[Co(NO_3)_2 \cdot 6H_2O]$ and Pd (II) nitrate using an appropriate quantity to achieve incipient wetness (ca. 1.2 ml/g) with the desired loading of Co and Pd. Next, the catalyst precursor was dried in an oven for 5 hours at 115° C. with moderate stirring. Then the dried catalyst was calcined in air by raising its temperature at a heating rate of 1° C./min to 300° C. and holding for 2 hours.
Precursors used for 150 g reduced catalyst:

| Chemical Precursor | Chemical Formula | Metal Conc. in Precursor (wt %) | Metal Loading in Reduced Catalyst (wt %) | Precursor Amount (g) |
|---|---|---|---|---|
| Cobalt Nitrate | $Co(NO_3)_2 \cdot 6H_2O$ | 20.2566 | Co: 20 | 148.10 |
| Palladium (II) Nitrate | $Pd(NO_3)_2 \cdot xH_2O$ | 40.53 | Pd: 0.5 | 1.85 |
| Calcined γ-alumina | $Al_2O_3$ | — | $Al_2O_3$: 79.5 | 119.25 |

Catalyst Formulation EI.32
Composition: 20 pbw Co
  1.0 pbw Pd
  79.0 pbw γ-alumina support
Amount produced: 300 g
Preparation Procedure:
Vista CATAPAL B γ-alumina was calcined at 500° C. for 10 hours (1°/min to 500° C.) and sieved to >38 microns and <88 microns (400–170 mesh). Then the support was impregnated with an aqueous solution of Co nitrate $[Co(NO_3)_2 \cdot 6H_2O]$ and Pd (II) nitrate using an appropriate quantity to achieve incipient wetness (ca. 1.2 ml/g) with the desired loading of Co and Pd. Next, the catalyst precursor was dried in an oven for 5 hours at 115° C. with moderate stirring. Then the dried catalyst was calcined in air by raising its temperature at a heating rate of 1° C./min to 300° C. and holding for 2 hours.
Precursors used for 300 g catalyst:

| Chemical Precursor | Chemical Formula | Metal Conc. in Precursor (wt %) | Metal Loading in Reduced Catalyst (wt %) | Precursor Amount (g) |
|---|---|---|---|---|
| Cobalt Nitrate | $Co(NO_3)_2 \cdot 6H_2O$ | 20.2566 | Co: 20 | 148.10 |
| Palladium (II) Nitrate | $Pd(NO_3)_2 \cdot xH_2O$ | 40.53 | Pd: 1.0 | 3.70 |
| Calcined γ-alumina | $Al_2O_3$ | — | $Al_2O_3$: 79.5 | 118.50 |

Catalyst Formulation EI.33
Composition: 20 pbw Co
  2.0 pbw Pd
  78.0 pbw γ-alumina support
Amount produced: 150 g
Preparation Procedure:
Vista CATAPAL B γ-alumina was calcined at 500° C. for 10 hours (1° C./min to 500° C.) and sieved to >38 microns and <88 microns (400–170 mesh). Then the support was impregnated with an aqueous solution of Cobalt nitrate [Co(NO$_3$)$_2$ . 6H$_2$O] and Palladium (II) nitrate [Pd(NO$_3$)$_2$ . xH$_2$O] using an appropriate quantity to achieve incipient wetness (ca 1.2 ml/g) with the desired loading of Co and Pd. Next, the catalyst precursor was dried in an oven for 5 hours at 115° C. with moderate stirring and calcined in air by raising its temperature at a heating rate of 1° C./min to 300° C. and holding for 2 hours.

Precursors used for 150 g reduced catalysts:

| Chemical Precursor | Chemical Formula | Metal Conc. in Precursor (wt %) | Metal Loading in Reduced Catalyst (wt %) | Precursor Amount (g) |
| --- | --- | --- | --- | --- |
| Cobalt Nitrate | Co(NO$_3$)$_2$.6H$_2$O | 20.2566 | Co: 20 | 148.10 |
| Palladium (II) Nitrate | Pd(NO$_3$)$_2$.xH$_2$O | 40.53 | Pd: 2.0 | 7.40 |
| Calcined γ-alumina | Al$_2$O$_3$ | — | Al$_2$O$_3$: 78.0 | 117.00 |

Catalyst Formulation EI.34
Composition: 30 pbw Co
  1.5 pbw Pd
  68.5 pbw γ-alumina support
Amount produced: 150 g
Preparation Procedure:
CATAPAL B γ-alumina was calcined at 500° C. for 10 hours (1° C./min to 500° C.) and sieved to >38 microns and <88 microns (400–170 mesh). Then the support was impregnated in 2 steps with an aqueous solution of Co nitrate [Co(NO$_3$)$_2$ . 6H$_2$O] and Pd (II) nitrate [Pd(NO$_3$)$_2$ . xH$_2$O] using, in the first step, an appropriate quantity to achieve incipient wetness (ca 1.2 ml/g) with 60% of the desired loading of Co and Pd. Next, the catalyst precursor was dried in an oven for at least 5 hours at 115° C. with moderate stirring and calcined in air by raising its temperature at a heating rate of 1° C./min to 300° C. and holding for 2 hours. In the second step, the calcined catalyst was impregnated with the remaining 40% of Co and Pd nitrate solution and the drying and calcination procedures were repeated.

Precursors used for 150 g reduced catalyst:

| Chemical Precursor | Chemical Formula | Metal Conc. in Precursor (wt %) | Metal Loading in Reduced Catalyst (wt %) | Precursor Amount (g) |
| --- | --- | --- | --- | --- |
| Cobalt Nitrate | Co(NO$_3$)$_2$.6H$_2$O | 20.2566 | Co: 30 | 222.15 |
| Palladium (II) Nitrate | Pd(NO$_3$)$_2$.xH$_2$O | 40.53 | Pd: 1.5 | 5.55 |
| Calcined γ-alumina | Al$_2$O$_3$ | — | Al$_2$O$_3$: 68.5 | 102.75 |

EXAMPLE 2

The following catalysts were prepared and activated as indicated:

Co.005: 20 pbw Co
  80 pbw γ-alumina support
Preparation Procedure:
Calcined the γ-alumina (Vista CATAPAL B) at 500° C. for 10 hrs. Presieved to >38 microns (400–0 mesh). Impregnated the support with an aqueous solution of Co nitrate [Co(NO$_3$)$_2$ . 6H$_2$O] using an appropriate quantity to achieve incipient wetness (ca. 1.2 ml/g) with the desired loading of Co. Dried the catalyst precursor in an oven for 5 hrs at 115° C. with moderate stirring. Calcined the dried catalyst in air by raising its temperature at a heating rate of ca. 1° C./min to 300° C. and holding for 2 hrs.
Reduction Procedure before Reaction:
  Reduced the catalyst in a pure hydrogen flow of 3000 cc/g per hr by heating at 1° C./min to 350° C. and holding for 10 hrs.

Co.053: 20 pbw Co
  0.5 pbw Ru
  79.5 pbw γ-alumina support
Preparation Procedure:
Calcined the γ-alumina support (Vista CATAPAL B) at 500° C. for 10 hrs. Presieved to >38 microns (400–0 mesh). Impregnated the support with an aqueous solution of Co nitrate [Co(NO$_3$)$_2$ . 6H$_2$O] and Ru nitrosyl nitrate using an appropriate quantity to achieve incipient wetness (ca. 1.2 ml/g) with the desired loading of Co and Ru. Dried the catalyst precursor in an oven for 5 hrs at 115° C. with moderate stirring. The dried catalyst was then calcined in air by raising its temperature at a heating rate of ca. 1° C./min to 300° C. and holding for 2 hrs.
Reduction Procedure before Reaction:
  Reduced the catalyst in a pure hydrogen flow of 3000 cc/g per hr by heating at 1° C./min to 350° C. and holding for 10 hrs.

Co.067: 20 pbw Co
  2.0 pbw Pd
  78 pbw γ-alumina support
Preparation Procedure:
Calcined the γ-alumina support (Vista CATAPAL B) at 500° C. for 10 hrs. Presieved to >38 microns (400–0 mesh). Impregnated the support with an aqueous solution of Co nitrate [Co(NO$_3$)$_2$ . 6H$_2$O], and Pd (II) nitrate using an appropriate quantity to achieve incipient wetness with the desired loadings of Co and Pd. Dried the catalyst precursor in an oven for 5 hrs at 115° C. with moderate stirring. The dried catalyst was then calcined in air by raising its temperature at a heating rate of ca. 1° C./min to 300° C. and holding for 10 hrs.
Reduction Procedure before Reaction:
  Reduced the catalyst in a pure hydrogen flow of 3000 cc/g per hr by heating at 1° C./min to 350° C. and holding for 10 hrs.

Co.068: 20 pbw Co
  1.0 pbw Pd
  79 pbw γ-alumina support
Preparation Procedure:
Calcined the γ-alumina support (Vista CATAPAL B) at 500° C. for 10 hrs. Presieved to >38 microns (400–0 mesh). Impregnated the support with an aqueous solution of Co nitrate [Co(NO$_3$)$_2$ . 6H$_2$O], and Pd (II) nitrate using an appropriate quantity to achieve incipient wetness (ca. 1.2 ml/g) with the desired loadings of Co, and Pd. Dried the catalyst precursor in an oven for 5 hrs at 115° C. with moderate stirring. The dried catalyst was then calcined in air by raising its temperature at a heating rate of ca. 1° C./min to 300° C. and holding for 10 hrs.
Reduction Procedure before Reaction:
  Reduced the catalyst in a pure hydrogen flow of 3000 cc/g per hr by heating at 1° C./min to 350° C. and holding for 10 hrs.

EXAMPLE 3

As presented in Table 1, tests conducted using a palladium-promoted Co catalyst revealed that, in a fixed bed reactor, significant activity enhancement (i.e., more than a two-fold increase in activity above that of an unpromoted Co/Al$_2$O$_3$ catalyst) may be provided by addition of palladium. Further, the activity results obtained with the same palladium-promoted cobalt catalyst in a slurry bubble column reactor were unexpectedly comparable to those obtained using a ruthenium-promoted catalyst. Thus, the surprising activity improvement provided by palladium applies to both fixed bed and SBC reactor applications. The catalysts tested in this example were prepared and activated as described in Example 2.

TABLE 1

Palladium Promoted Cobalt Catalyst Performance

| Catalyst No. | Support | Promoter (wt %/atom.ratio) | Reactor | Run No. | Activity (g-HC/g-cat./h) 220° C. | 240° C. |
|---|---|---|---|---|---|---|
| Co.005 | Al$_2$O$_3$ | none | FB | 10 | 0.106 | 0.239 |
| Co.053 | Al$_2$O$_3$ | Ru (0.5/0.015) | FB | 3 | 0.453 | 0.647 |
| Co.068 | Al$_2$O$_3$ | Pd (1.0/0.027) | FB | 2 | 0.250 | 0.420 |
| Co.005 | Al$_2$O$_3$ | none | SBCR | M3-15-1 | 0.53 | 1.34 |
| Co.053 | Al$_2$O$_3$ | Ru (0.5/0.015) | SBCR | M4-29-1 | 0.59 | 1.19 |
| Co.068 | Al$_2$O$_3$ | Pd (1.0/0.027) | SBCR | M3-49-1 | — | 1.26 |

Reaction conditions - InFixedBed: P = 1 atm, T = 220–240° C., H$_2$/CO = 2; inSBCR: Catalyst weight: ca. 15 g, screened thru 150 × 400 mesh, calcined and reduced externally, T = 220–240° C., P = 450 psi, H$_2$/CO = 2, Total flow rate: ca. 15 L/min, Diluent: N$_2$: ca.60%. Error in rate measurements = ±5%.

In addition, temperature programmed reduction studies conducted by Applicants confirm that palladium addition has a positive effect on cobalt reducibility, similar to the positive effect provided by ruthenium.

Thus, the present invention is well adapted to carry out the objects and attain the ends and advantages mentioned above, as well as those inherent therein. While the invention has been described with a certain degree of particularity, it is manifest that many changes may be made without departing from the spirit and scope of this disclosure. It is understood that the invention is not limited to the embodiments set forth herein for purposes of exemplification.

What is claimed is:

1. A process for Fischer-Tropsch synthesis comprising the steps of:
   (a) co-impregnating a γ-alumina support with cobalt and palladium by totally aqueous co-impregnation to obtain a palladium-promoted, cobalt-on-alumina catalyst comprising from about 10 to about 65 parts by weight (pbw) of said cobalt and from about 0.25 to about 9 pbw of said palladium per 100 pbw of said γ-alumina support, said cobalt and said palladium forming a dispersed catalytic phase wherein said palladium is in intimate contact with said cobalt; and
   (b) reacting a Fischer-Tropsch synthesis gas in the presence of said palladium-promoted, cobalt-on-alumina catalyst in a continuous reaction system.

2. The process of claim 1 wherein said γ-alumina support is a support which has been produced from boehmite using a spray drying and calcination process effective to yield a spheroidal support material having a BET surface area of from about 200 to about 260 m$^2$/g and an average particle size in the range of from about 10 μm to about 150 μm.

3. The process of claim 1 wherein said palladium-promoted, cobalt-on-alumina catalyst comprises from about 17 to about 45 pbw of said cobalt per 100 pbw of said γ-alumina support.

4. The process of claim 1 wherein said palladium-promoted, cobalt-on-alumina catalyst comprises about 20 pbw of said cobalt, about 1 pbw of said palladium, and about 79 pbw of said γ-alumina support.

5. The process of claim 1 further comprising the step, prior to step (b), of reducing said palladium-promoted, cobalt-on-alumina catalyst in a reducing gas consisting essentially of from about 1% to 100% by volume hydrogen and from 0% to about 99% by volume inert gas.

6. The process of claim 5 wherein said inert gas consists essentially of nitrogen.

7. The process of claim 1 wherein said palladium-promoted, cobalt-on-alumina catalyst consists essentially of said γ-alumina support, said cobalt, and said palladium.

8. The process of claim 1 wherein step (a) is completed prior to beginning step (b) and said process further includes the step of placing said palladium-promoted, cobalt-on-alumina catalyst formed in step (a) in said continuous reaction system.

9. A process for Fischer-Tropsch synthesis comprising the step of reacting a Fischer-Tropsch synthesis gas in a continuous reaction system in the presence of a palladium-promoted, cobalt-on-alumina catalyst produced by co-impregnating a γ-alumina support with cobalt and palladium by totally aqueous co-impregnation such that said palladium-promoted, cobalt-on-alumina catalyst comprises from about 10 to about 65 parts by weight (pbw) of said cobalt and from about 0.25 pbw to about 9 pbw of said palladium per 100 pbw of γ-alumina support, said cobalt and said palladium forming a dispersed catalytic phase wherein said palladium is in intimate contact with said cobalt.

10. The process of claim 9 wherein said γ-alumina support is a support which has been produced from boehmite using spray drying and calcination process effective to yield a spheroidal support material having a BET surface area of from about 200 to about 260 m$^2$/g and an average particle size in the range of from about 10 μm to about 150 μm.

11. The process of claim 9 wherein said palladium-promoted, cobalt-on-alumina catalyst comprises from about 17 to about 45 pbw of said cobalt per 100 pbw of said γ-alumina support.

12. The process of claim 9 wherein said palladium-promoted, cobalt-on-alumina catalyst comprises about 20 pbw of said cobalt, about 1 pbw of said palladium, and about 79 pbw of said γ-alumina support.

13. The process of claim 9 further comprising the step, prior to said step of reacting, of reducing said palladium-promoted, cobalt-on-alumina catalyst in a reducing gas consisting essentially of from about 1% to 100% by volume hydrogen and from 0% to about 99% by volume inert gas.

14. The process of claim 13 wherein said inert gas consists essentially of nitrogen.

15. The process of claim 9 wherein said continuous reaction system is one of a fixed bed reaction system and a slurry bubble column reaction system.

16. A process for Fischer-Tropsch synthesis comprising the step of reacting a Fischer-Tropsch synthesis gas in the presence of a palladium-promoted, cobalt-on-alumina catalyst produced by co-impregnating a γ-alumina support with cobalt and palladium by totally aqueous co-impregnation such that said palladium-promoted, cobalt-on-alumina catalyst consists essentially of from about 10 to about 65 parts by weight (pbw) of said cobalt and from about 0.25 pbw to about 9 pbw of said palladium per 100 pbw of said γ-alumina support, said cobalt and said palladium forming a dispersed catalytic phase wherein said palladium is in intimate contact with said cobalt.

17. The process of claim 16 wherein said γ-alumina support is a support which has been produced from boehmite using spray drying and calcination processes effective to yield a spheroidal support material having a BET surface area of from about 200 to about 260 m$^2$/g and an average particle size in the range of from about 10 µm to about 150 µm.

18. The process of claim 16 wherein said palladium-promoted, cobalt-on-alumina catalyst consists essentially of about 20 pbw of said cobalt, about 1 pbw of said palladium, and about 79 pbw of said γ-alumina support.

19. The process of claim 16 further comprising the step, prior to said step of reacting, of reducing said palladium-promoted, cobalt-on-alumina catalyst in a reducing gas consisting essentially of from about 1% to 100% by volume hydrogen and from 0% to about 99% by volume inert gas.

20. The process of claim 19 wherein said inert gas consists essentially of nitrogen.

* * * * *